United States Patent [19]

Scheubeck et al.

[11] 4,192,849

[45] Mar. 11, 1980

[54] PRESSURE DIGESTER

[75] Inventors: Egmont Scheubeck; Johann Gehring, both of Erlangen, Fed. Rep. of Germany

[73] Assignee: Siemens Aktiengesellschaft, Munich, Fed. Rep. of Germany

[21] Appl. No.: 960,790

[22] Filed: Nov. 15, 1978

[30] Foreign Application Priority Data

Nov. 28, 1977 [DE] Fed. Rep. of Germany ....... 2753019

[51] Int. Cl.² .................... B01J 3/04; B65D 41/04; B65D 45/02

[52] U.S. Cl. ................... 422/242; 23/230 PC; 220/314; 220/329; 220/345; 422/74; 422/78; 422/102; 422/164; 422/184

[58] Field of Search .................... 422/74, 78, 102, 51, 422/164, 184, 242, 307, 295, 296, 118; 23/230 PC; 220/314, 345, 329, 288

[56] References Cited

U.S. PATENT DOCUMENTS

| | | | |
|---|---|---|---|
| 976,969 | 11/1910 | Williams | 422/242 |
| 1,014,192 | 1/1912 | Williams | 422/242 |
| 2,227,712 | 1/1941 | Hackley | 220/314 |
| 3,131,925 | 5/1964 | Coats | 220/314 X |
| 3,147,068 | 9/1964 | Castle et al. | 422/296 X |
| 3,371,986 | 3/1968 | Brown | 422/295 X |
| 3,386,206 | 6/1968 | Loveless | 220/345 X |
| 3,511,593 | 5/1970 | Thomas et al. | 422/295 |
| 3,681,008 | 8/1972 | Black | 220/345 X |
| 3,804,288 | 4/1974 | Piegza | 220/329 |
| 4,094,640 | 6/1978 | Iwantscheff et al. | 422/78 X |

*Primary Examiner*—Barry S. Richman
*Attorney, Agent, or Firm*—Kenyon & Kenyon

[57] ABSTRACT

A stationary pressure digester for digesting biomaterials with a fast acting closure designed as an easily movable cover carriage with a lower pressure take up plate, an upper pressure take up plate and a closing threaded plug in one of said plates. The pressure take up plates are connected by necked-down bolts and spacer sleeves and the closing nut has a thread with a large pitch and a large area permitting a pressure tight closure which permits moving the closure cover as well as opening and closing the pressure digester fast and easily.

11 Claims, 4 Drawing Figures

PRESSURE DIGESTER

BACKGROUND OF THE INVENTION

This invention relates to pressure digesters for digesting biomaterials in general and more particularly to a fast acting closure for a stationary pressure digester.

For the analytical determination of element traces and, in particular, for detecting traces of metals in biomaterials such as foodstuffs, a fairly large amount of sample material, e.g., meat, is digested in a short time in a combustion in oxygen under pressure, according to one proposed method (U.S. Pat. No. 4,094,640). For carrying out this method rapidly, a pressure digesting vessel which is simple to operate and, in particular, which can be opened and closed quickly and conveniently, is especially advantageous.

Commercially available laboratory autoclaves with a capacity of, for instance, 1.5 l, take always about 15 to 20 minutes for opening or closing the device without elaborate mechanical equipment. A fairly large number of tightening nuts must be screwed on or off in the process. In addition, the relatively heavy cover must be lifted off and replaced by hand. On the other hand, for autoclaves which can be opened and closed quickly and simply, elaborate mechanical equipment is necessary, such as pneumatically or electrically operated devices.

SUMMARY OF THE INVENTION

It is an object of the present invention to provide a pressure digester which is free of the disadvantages of the known devices as far as immediate closing and opening of the pressure digesting device or equipment is concerned. The objective is, in particular, to ensure trouble free closing and reliable as well as fast opening, after the digestion is completed, with simply designed and reliably acting means and without elaborate supplemental equipment.

According to the present invention, this problem is solved with a pressure digester in which the closure of a pressure digesting vessel, which is firmly mounted on a base plate, is designed as an easily movable cover carriage comprising a lower pressure take up plate and an upper pressure take up plate, which are connected by necked-down bolts and spacer sleeves. A closure in the form of a threaded plug is disposed in the upper take up plate. With an axial lift of 1 mm, pressure tight closing of a pressure digesting vessel by the upper pressure take up plate is achieved. The closing threaded plug should have a thread with large pitch, preferably 4 mm, and should have a large area. An axial lift of 1 mm with a rotary movement of 45° is suitable. The large area geometry of the threaded plug prevents opening even at a low internal pressure. The closure is self-locking and thus constitutes a true safety closure. While the closure plug is shown as being located in the upper take up plate, it would be immediately obvious that one could use a closure plug mounted in the lower take up plate when dealing with a bottom-opening digester.

With a device according to the present invention, a pressure digesting vessel can be opened and closed in a few seconds. A further advantage is seen in the fact that a pressure tight closure of the pressure vessel is achieved by only a small rotation of the threaded plug. The opening and closing operations do not depend on special actuating mechanisms. The design of the device according to the present invention is extremely simple, but its operation is absolutely reliable and error free.

According to a further feature of the present invention, the pressure vessel has an O-ring and a support ring, whereby a particularly pressure proof, gastight seal, which can be opened easily when the pressure is relieved, can be achieved upon closing.

According to a preferred embodiment, the pressure digesting vessel is firmly mounted on the base plate by two support bars via two support blocks.

The upper and lower pressure take up plates of the cover, which is designed as a carriage, can be moved over or under, respectively, the rigidly mounted pressure vessel. The pressure on the pressure vessel is transmitted via the upper pressure take up plate with the threaded plug and the lower pressure take up plate to the necked-down bolts and the spacer sleeves. It is advisable to use only a few, preferably four, necked-down bolts and spacer sleeves.

A particularly gastight closure is achieved with a device, the cover carriage of which forms a compact unit consisting of a lower pressure take up plate, an upper pressure take up plate, four necked-down bolts with nuts and four spacer sleeves.

DETAILED DESCRIPTION OF THE INVENTION

Figure 1:
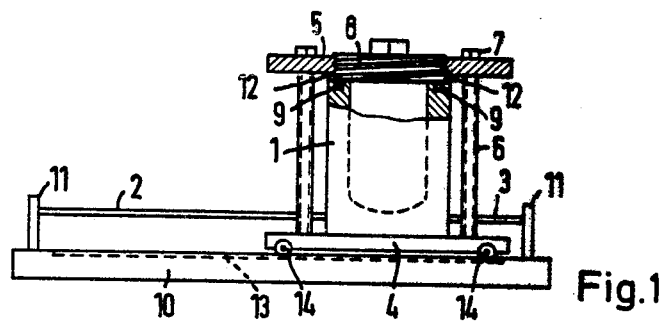
FIG. 1 is a longitudinal cross section of a pressure digester according to the present invention in the closed condition.
Figure 3:
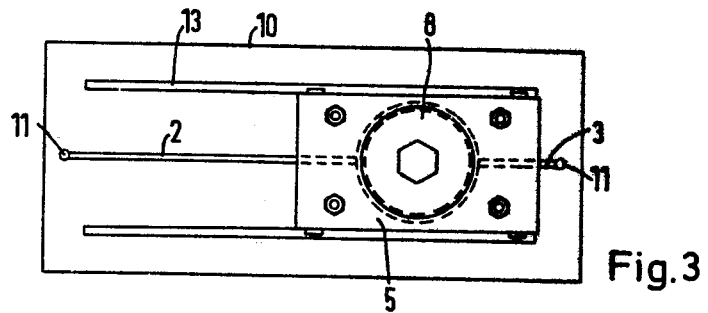
FIG. 3 is a top view of the device of FIG. 1.

The pressure digester shown in FIGS. 1 to 4 includes a pressure digesting vessel 1 which is firmly connected to a base plate 10 by support bars 2 and 3 mounted on two support blocks 11. With this mounting the bottom of vessel 1 is spaced from base plate 10. The digesting vessel is closed off in a gastight manner with a cover carriage 15 which is movable on rollers 14 and includes a lower pressure take up plate 4, an upper pressure take up plate 5, four necked-down bolts with nuts 7 and four spacer sleeves 6, to constitute a compact unit. Disposed in the upper pressure plate 5 is a closure in the form of a threaded plug 8 with a screw pitch of 4 mm. The rollers of the cover carriage are guided in guide slots 13.

Figure 2:
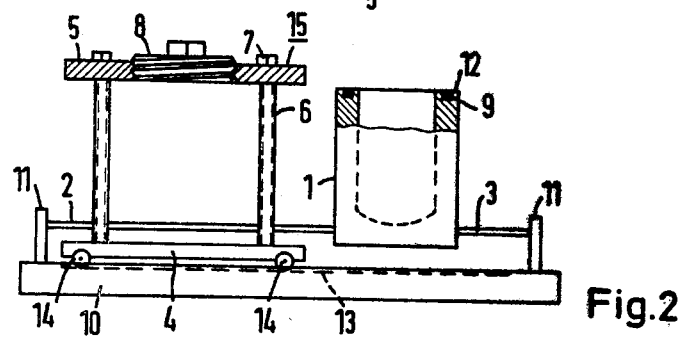
FIG. 2 is a longitudinal cross section of the pressure digester of FIG. 1 in an open condition.
Figure 4:
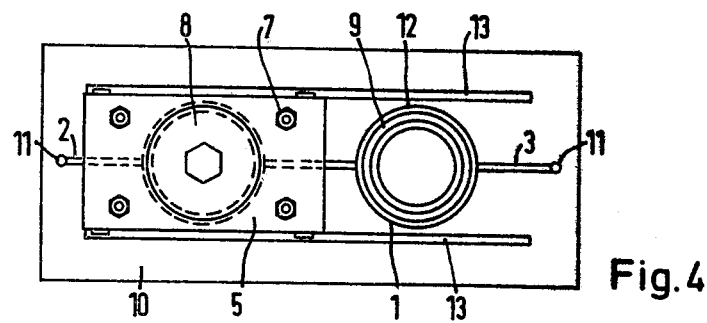
FIG. 4 is a top view of the device of FIG. 2.

As best illustrated by FIGS. 2 and 4, an O-ring 9 is placed inside a support ring 12 to achieve a particularly pressure tight closure which can at the same time be opened easily in the pressure relieved condition. The individual parts of the device can consist of high alloy steel. When the carriage 15 is moved so that the pressure digesting vessel 1 is centered between the two pressure take up plates 4 and 5, as shown on FIGS. 1 and 3, then a pressure tight closure is accomplished between the O-ring 9 and the support ring 12 and threaded plug 8 when threaded plug 8 is rotated by about 45°.

After digesting in vessel 1, threaded plug 8 is rotated in the opposite direction and the cover carriage moved to the position shown in FIGS. 2 and 4.

The illustrated embodiment is intended for digesting meat samples (weight about 25 g), for the analytical determination of metal traces. The device is equally well suited for digesting samples of organs such as liver, kidney, lung and other foodstuffs of any kind such as fats, oils, legumes and dairy products for trace analyses of metals such as Hg, As, Pb and Cd.

What is claimed is:

1. A pressure digester with a fast action closure for digesting biomaterials, comprising:
   (a) a base;
   (b) a pressure digesting vessel firmly mounted to said base; and
   (c) a cover carriage movable on said base between a position wherein it is in alignment with said vessel and a position where it is laterally spaced from said vessel and comprising a lower pressure take up plate, an upper pressure take up plate, necked-down bolts and spacer sleeves connecting said take up plates, and a closure in the form of a threaded plug disposed in one of said cover plates, whereby said cover carriage may be moved into alignment with said vessel with said lower take up plate below and said upper take up plate above said vessel and said threaded plug turned to close said vessel in a pressure tight manner.

2. A pressure digester according to claim 1, wherein said pressure digesting vessel is mounted on said base by mounting means comprising two support bars extending laterally from said vessel and two support blocks mounted to said base and supporting said bars.

3. A pressure digester according to claim 1, wherein four spacer sleeves and four necked-down bolts with nuts are provided.

4. A pressure digester according to claim 1, wherein said threaded plug is disposed in said upper take up plate and wherein four necked-down bolts with nuts and four spacer sleeves are provided.

5. A pressure digester according to claim 1, wherein said threaded plug has a thread with large pitch.

6. A pressure digester according to claim 5, wherein said threaded plug has a large area.

7. A pressure digester with a fast action closure for digesting biomaterials, comprising:
   (a) a base plate;
   (b) a pressure digesting vessel;
   (c) means for mounting said vessel to said base in such a manner that it is spaced from said base plate with free access to the bottom of said vessel;
   (d) a cover carriage movable on said base plate between a position where it is in alignment with said vessel and a position where it is laterally spaced from said vessel, comprising:
      (i) a lower pressure take up plate;
      (ii) an upper pressure take up plate;
      (iii) a closure in the form of a threaded plug threaded into said upper pressure take up plate; and
      (iv) necked-down bolts with nuts and spacer sleeves connecting said upper and lower take up plates, whereby said cover carriage may be moved into alignment with said vessel with said lower take up plate below and said upper take up plate above said vessel and said threaded plug turned to close said vessel in a pressure tight manner.

8. Apparatus according to claim 7 wherein said means for mounting comprise:
   (a) first and second support blocks at opposite ends of said base plate; and
   (b) first and second laterally extending rods connecting said vessel to said first and second support blocks respectively.

9. A pressure digester according to claim 8, wherein said threaded plug has a thread with large pitch.

10. A pressure digester according to claim 9, wherein said threaded plug has a large area.

11. Apparatus according to claim 10 and further including:
    (a) a support ring at the top of said vessel; and
    (b) an O-ring inside said support ring.

* * * * *